(12) United States Patent
Mangano et al.

(10) Patent No.: US 7,172,577 B2
(45) Date of Patent: Feb. 6, 2007

(54) GUIDEWIRE LOCKING DEVICE AND METHOD

(75) Inventors: Michael J. Mangano, Tokyo (JP); Hisashi Noda, Hyogo-prefecture (JP)

(73) Assignee: Boston Scientific Scimed, Inc., Maple Grove, MN (US)

( * ) Notice: Subject to any disclaimer, the term of this patent is extended or adjusted under 35 U.S.C. 154(b) by 228 days.

(21) Appl. No.: 10/217,317

(22) Filed: Aug. 9, 2002

(65) Prior Publication Data
US 2004/0030290 A1 Feb. 12, 2004

(51) Int. Cl.
*A61M 5/178* (2006.01)
(52) U.S. Cl. .................................. 604/164.04
(58) Field of Classification Search ........... 604/164.04, 604/164.13, 165.01, 165.02, 165.04, 158, 604/95.04
See application file for complete search history.

(56) References Cited

U.S. PATENT DOCUMENTS 5,159,861 A 11/1992 Anderson
6,096,009 A * 8/2000 Windheuser et al. .. 604/165.01
6,190,352 B1 2/2001 Haarala et al.
6,312,404 B1 11/2001 Agro et al.
6,346,093 B1 2/2002 Allman et al.
6,569,151 B1 * 5/2003 Nash et al. ................. 604/533
6,746,466 B2 * 6/2004 Eidenschink et al. ....... 606/194
2002/0026149 A1 2/2002 Agro et al.

FOREIGN PATENT DOCUMENTS

WO WO 01/68177 A1 9/2001

* cited by examiner

*Primary Examiner*—Catherine S. Williams
(74) *Attorney, Agent, or Firm*—Crompton, Seager & Tufte, LLC

(57) ABSTRACT

A locking device (21) is provided that is fixedly mounted to a catheter (34) and used to frictionally secure a guidewire (36) to the catheter (34) so that the guidewire (36) and catheter (34) may be advanced together. In one embodiment of the present invention, the locking device (21) comprises a J-shaped catch (22) integrally formed with a guidewire introducer (10) fixedly mounted to the catheter shaft (38). Once the guidewire (36) has been inserted into the shaft (38) via the guidewire introducer (10), the operator may insert the guidewire into the J-shaped catch (22). The guidewire (36) can then be released by sliding the guidewire (36) out of the J-shaped catch (22).

3 Claims, 4 Drawing Sheets

GUIDEWIRE LOCKING DEVICE AND METHOD

FIELD OF THE INVENTION

The present invention relates to a guidewire locking device for use in catheter procedures within the human anatomy, and methods of using the same. More particularly, the present invention relates to a guidewire locking device that locks a guidewire directly to the catheter, so that when locked, the guidewire and catheter can be moved together.

BACKGROUND OF THE INVENTION

Endoscopic procedures for treating abnormal pathologies within the alimentary canal system and biliary tree (including the biliary, hepatic, and pancreatic ducts) are increasing in number. The endoscope provides access to the general area of a desired duct using direct visualization. However, the duct itself must be navigated using a catheter in conjunction with fluoroscopy and guidewires. Catheters are known for treatment of targeted anatomical regions. Known methods and devices for using biliary catheters for accessing the biliary tree for performing catheter procedures are disclosed in Weaver et al., U.S. Pat. No. 5,397,302, Karpiel, U.S. Pat. No. 5,320,602, and Windheuser et al., U.S. Pat. No. 6,096,099, each of which is herein incorporated by reference. In general, for treatment of an abnormal pathology within a patient's biliary tree, an endoscope is first introduced into the mouth of the patient. The endoscope includes a proximal end and a distal end, and has a lumen extending longitudinally between the proximal and distal ends. The endoscope is guided through the patient's alimentary tract or canal until an opening at the distal end of the endoscope is proximate the area to receive treatment. At this point, the endoscope allows other components, such as a catheter, to access the targeted area.

For visualization or treatment within the biliary tree, the distal end of the endoscope is positioned proximate to the papilla of vater leading to the common bile duct and the pancreatic duct. A catheter is guided through the lumen of the endoscope until a distal tip of the catheter emerges from the opening at the distal end of the endoscope. The distal end of the catheter is then guided to the orifice to the papilla of vater (located between the sphincter of oddi) leading to the common bile duct and the pancreatic duct. A guidewire may be used in conjunction with the catheter to facilitate accessing a desired location within the biliary tree. This is known as guidewire cannulation. The guidewire is inserted in an opening at a proximal end of the catheter and guided through the catheter until it emerges from the distal end of the catheter. In order to properly position the guidewire and the catheter during this process, an operator may separate the guidewire from the catheter and control the guidewire separately. In addition, the operator will often extend the guidewire a few millimeters, e.g., 1 mm to 5 mm, outside of the catheter and advance the two together. This provides even more of a tapered system to advance into small openings, sphincters (that are contracting or opening) and through strictures. However, if the guidewire meets resistance, it may be pushed back into the catheter, requiring the operator to attempt to manually pinch both the guidewire and the catheter together. Unfortunately, manually pinching the guidewire and catheter together has proven unreliable and cumbersome for the operator. Accordingly, a locking device is desired whereby the operator can selectively secure the guidewire to the catheter during guidewire cannulation in order to help advance the guidewire and catheter together when resistance is met or advance the guidewire and catheter separately, if desired. Further, a locking device is desired that frees the operator's hands for other tasks.

SUMMARY OF THE INVENTION

In accordance with the present invention, a locking device is provided that is fixedly attached to an elongated medical tube, such as a catheter. The locking device comprises a catch for selectively receiving an elongated medical member, such as a guidewire or another catheter, and frictionally securing the elongated member to the elongated medical tube so that they may be advanced simultaneously. The catch comprises an entry end and a locking end. The entry end of the catch may be positioned parallel to the elongated medical tube, at an acute angle relative to the tube, or at substantially a right angle relative to the tube.

In yet other embodiments of the present invention, the locking device further comprises a hub fixedly attached to the elongated medical tube, wherein the hub has a slot defined therein for aligning with an access port in the tube. The hub comprises a sleeve which surrounds the elongated medical tube and a flange protruding outwardly from the sleeve so that the slot defined in the hub runs through the sleeve and the flange. A catch is connected to the hub for selectively receiving the elongated member via the slot and frictionally securing the elongated member to the elongated medical tube. To further guide the elongated member from the slot to the catch, a guiding tab is located between the catch and the flange. In yet other embodiments of the present invention, a plurality of catches are connected to the hub for selectively receiving the elongated member and frictionally securing it to the elongated medical tube. Finally, in accordance with yet other embodiments of the present invention, a method for locking a guidewire to a catheter is provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
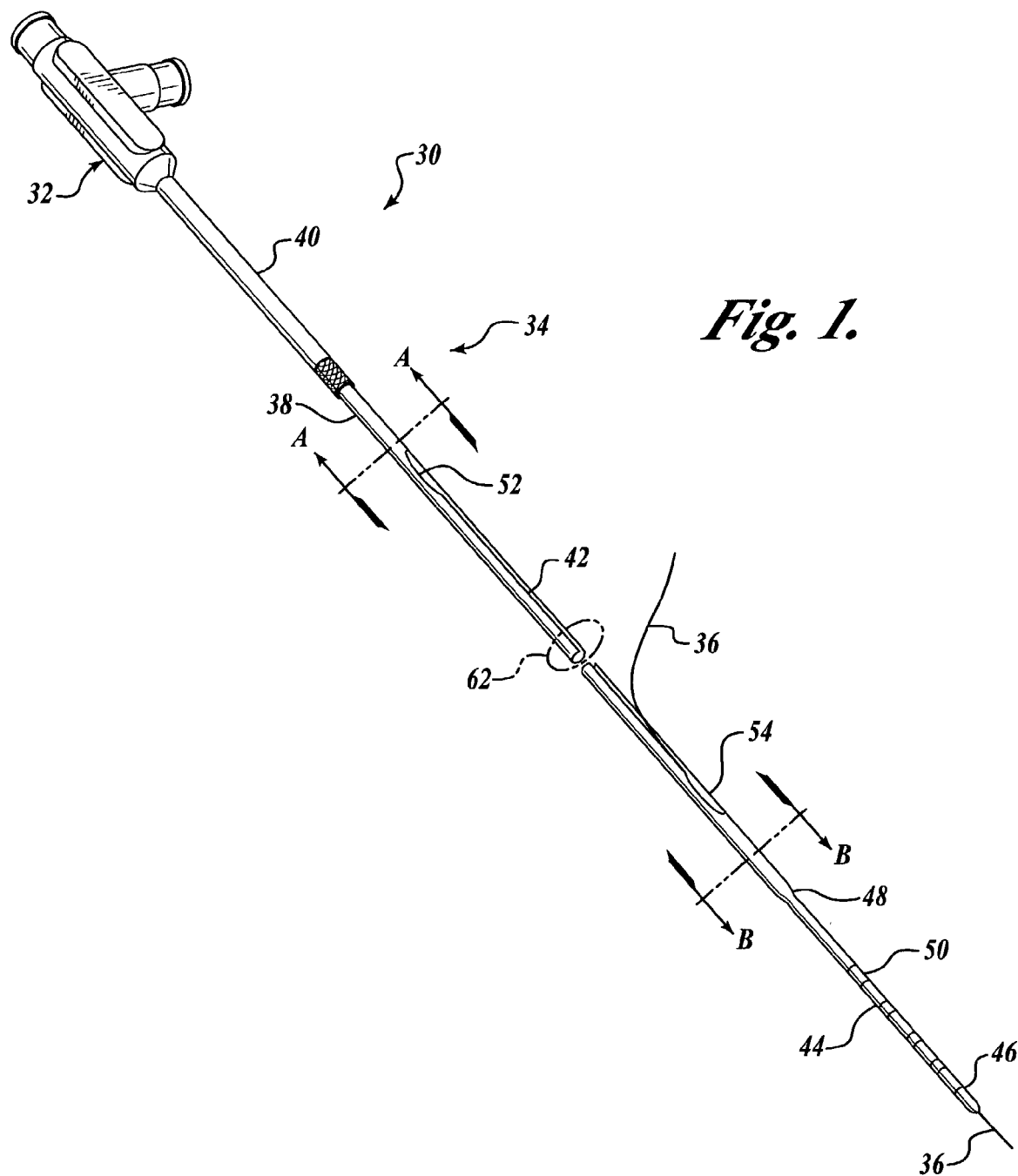
FIG. 1 is a perspective view of a catheter formed in accordance with the present invention having a C-shaped channel and guidewire lumen for directing a guidewire along its shaft and for facilitating rapid catheter exchange.

FIG. 1 shows a perspective view of a catheter assembly 30 formed in accordance with the present invention. Catheter assembly 30 is used in catheter procedures for accessing targeted anatomical regions through the alimentary canal and biliary tree. The depicted catheter includes features which allow rapid exchange of a catheter by a single operator. Catheter assembly 30 includes a catheter hub assembly 32 and a catheter 34, having a guidewire 36 passing through a portion thereof. Catheter 34 includes a shaft 38, which in general terms has a proximal end 40, a C-channel 42, a distal tip region 44, a distal end 46 and various lumens described in greater detail below. Catheter hub assembly 32 is operably connected to proximal end 40 of shaft 38. Catheter hub assembly 32 is preferably configured to couple to ancillary devices allowing access to a lumen within shaft 38.

Shaft 38 is a generally tubular-shaped member having a generally uniform outer shape at proximal end 40. Shaft 38 may be sized for slideable passage through the lumen of an endoscope (not shown). Shaft 38 is preferably formed in an extrusion process. Shaft 38 may be formed of an extruded polymeric material. In one embodiment, the polymeric material is a polytetrafluoroethylene, polyether block amide, nylon or a combination or blend of these. Catheters which are contemplated include, but are not limited to, cannulas, sphincterotomes, cytology devices, and devices for stone retrieval and stent placement.

In one embodiment, shaft 38 further includes a distal taper 48 which tapers to distal tip region 44. Additionally, tip region 44 may include high contrast, color-coded distal markers 50. Finally, distal end 46 may be radiopaque for fluoroscopic visualization of distal tip region 44 during a catheter procedure.

C-channel 42 of shaft 38 extends between a first, proximal channel end 52 and a second, distal channel end 54. C-channel 42 serves to contain, but not necessarily constrain, guidewire 36, between channel proximal end 52 and channel distal end 54. The term "C-channel" refers to a channel shape tat allows radial removal of guidewire 36 from the channel 42, and need not be strictly in the shape of the letter C. For example, in other embodiments of the present invention, channel 42 may be generally "U" shaped. C-channel 42 in the depicted embodiment is sufficiently Large to allow radial guidewire 36 movement out of channel 42. Further, the diameter of the channel is substantially equal to or slightly larger than the diameter of the guidewire 36. Although it is recognized that proximal channel end 52 may be located at any location distal of proximal end 40 of shaft 38, channel distal end 54 is preferably located between 10 and 40 cm from distal end 46 of catheter shaft 38.

Figure 1A:
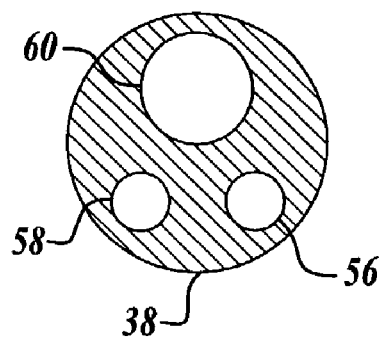
FIG. 1A is cross-sectional view of the catheter of FIG. 1 taken along the line 1A—1A.

Finally, as shown in FIG. 1A, which is a cross-sectional view of shaft 38 taken along line 1A—1A at a location proximal of channel proximal end 52, shaft 38 includes ancillary lumen 56, ancillary lumen 58 and guidewire lumen 60. Ancillary lumen 56 and ancillary lumen 58 extend longitudinally between proximal end 40 and distal end 48 of shaft 38. Ancillary lumen 56 and ancillary lumen 58 may be injection lumens, allowing for high contrast media flow capability for bubble-free opacification and for excellent visualization of a desired anatomical region. Additionally or alternatively, ancillary lumen 56 and/or ancillary lumen 58 may be used for or as part of other ancillary devices, such as a cutting wire lumen or a retrievable lumen.

Guidewire lumen 60 extends longitudinally between proximal end 40 and distal end 46 of shaft 38 in one embodiment. Further, guidewire lumen 60 is sized to receive guidewire 36. Guidewire lumen 60 may be a tubular member which is extruded integrally with catheter shaft 38, or alternatively, guidewire lumen 60 may be a separate tubular member which is coupled to catheter shaft 38. Although in one embodiment, the guidewire lumen 60 is a tubular member which is located proximate distal end 46 of catheter shaft 38, it is recognized that guidewire lumen 60 may be formed anywhere along shaft 38, may be an extension of shaft 38 coupled to distal end 46, or guidewire lumen 60 may run the entire length of shaft 38.

Figure 1B:
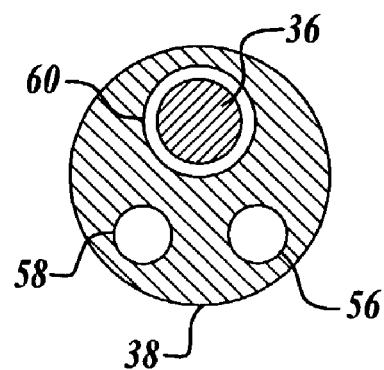
FIG. 1B is a cross-sectional view of the catheter with guidewire of FIG. 1 taken along the line 1B—1B.

Referring to FIG. 1B, a cross-sectional view of shaft 38 taken along line 1B—1B of FIG. 1 is shown. C-channel 42 serves as an access port for guidewire 36 to the guidewire lumen 60. More specifically, guidewire 36 may access guidewire lumen 60 at a point proximal channel distal end 54. Guidewire 36 extends within channel 42 to channel distal end 54, continuing within guidewire lumen 60 through distal tip region 44, and exiting through an opening in distal end 46.

Figure 1C:
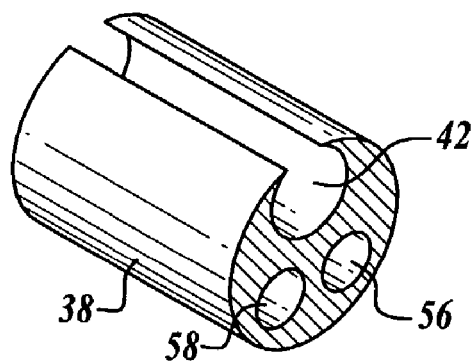
FIG. 1C is an enlarged fragmentary perspective view of the encircled catheter section of FIG. 1 at 1C.

Referring to FIG. 1C, a section of catheter shaft 38 having C-channel 42 taken from encircled section 62 of the catheter 34 is shown. The embodiment shown also includes ancillary lumens 56 and 58. Sections of shaft 38 proximate the channel proximal end 52 and distal channel distal end 54 contain guidewire lumen 60 in communication with C-channel 42. In one embodiment, C-channel 42 has an interior, closed-side geometry, substantially the same as the geometry of guidewire lumen 60.

Catheter shaft 38 may be configured such that C-channel 42 is defined separately from guidewire lumen 60. With this approach, guidewire lumen 60 is divided into two sections; a first section extending between proximal end 40 of shaft 38 and channel proximal end 52; and a second portion extending between channel distal end 54 and distal end 46 of shaft 38. Alternatively, the shaft can be configured to define guidewire lumen 60 as extending longitudinally between proximal end 40 and distal end 46 of shaft 38. In an alternative embodiment, between channel proximal end 52 and channel distal end 54, guidewire lumen 60 is integral with C-channel 42. In other words, guidewire lumen 60 defines a portion of C-channel 42 such that spacing between outer walls of C-channel 42 is equal to a diameter of guidewire lumen 60. Regardless of how guidewire lumen 60 and C-channel 42 are defined, C-channel 42 provides an access port to guidewire lumen 60 at a channel distal end 54. In this regard, channel distal end 54 can be enlarged to more easily direct guidewire 36 into guidewire lumen 60.

Figure 2:
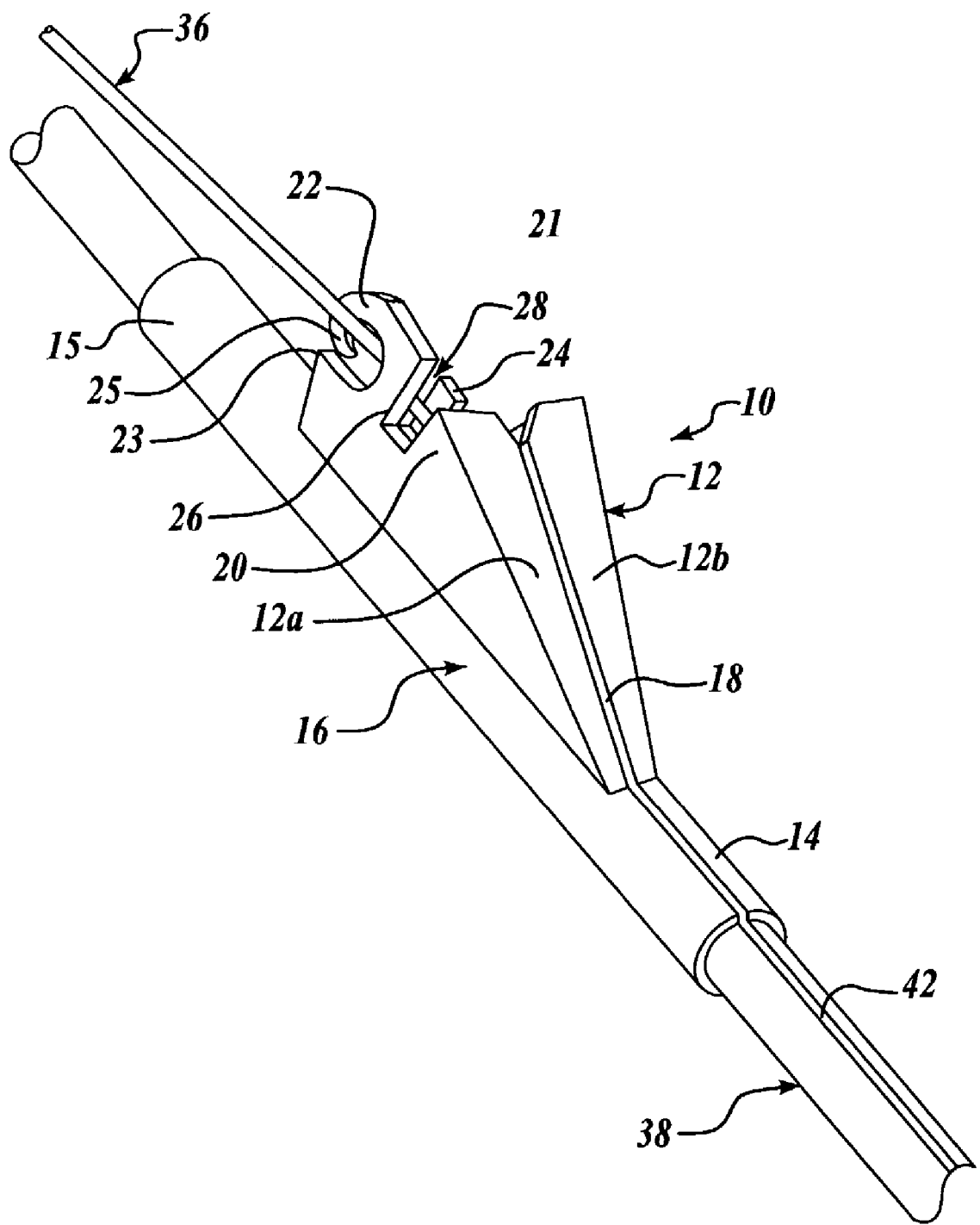
FIG. 2 is a perspective view of a guidewire introducer equipped with a locking device formed in accordance with the present invention which is fixedly mounted upon the catheter shown in FIG. 1.

As shown in FIG. 2, a guidewire introducer 10 having a guidewire lock 21 is mounted to the shaft 38 at the channel proximal end 52. The guidewire introducer 10 and lock 21 are formed of an acrylonitrile butadiene-styrene (ABS) plastic. Alternatively, any other semi-rigid or rigid, surgically safe material can be used. The guidewire introducer 10 is used to further ease the introduction of the guidewire 36 into guidewire lumen 60 via the C-channel 42. In one embodiment, the guidewire introducer 10 is fixedly mounted to the shaft 38, i.e., the guidewire introducer 10 is not removable from the shaft 38. Accordingly, when the guidewire 36 is secured to the guidewire lock 21, the catheter 34 and guidewire 36 can be advanced simultaneously without concern that the guidewire introducer 10 or guidewire lock 21 will move or become detached.

Guidewire introducer 10 comprises a hub formed from a sleeve 16 which surrounds the shaft 38 of the catheter 34 and a wedge-shaped flange 12 that protrudes outwardly from the sleeve 16 so as to form an inclined surface relative to the sleeve 16. A slot 18 for receiving the guidewire 36 is defined through the wedge-shaped flange 12 and a distal portion 14 of the sleeve 16. Accordingly, the guidewire introducer 10 is positioned relative to the shaft 38 so that the slot 18 is aligned with the C-channel 42 of the shaft 38. The slot 18 further serves to divide the wedge-shaped flange 12 into a first side 12a and a second side 12b. In accordance with one embodiment of the present invention, the guidewire lock 21 is integrally formed with the first side 12a of the wedge-shaped flange 12 at a proximal end 20 of the flange. However, those skilled in the art will appreciate that in other embodiments of the present invention, the guidewire lock 12 may be separately affixed to the guidewire introducer 10. By affixing the guidewire lock 21 to, or forming it integrally with, the guidewire introducer 10 (a component with which many catheters already are equipped), no further components need be added to the catheter. However, those skilled in the art will recognize that the guidewire lock 21 could be directly and permanently affixed to the shaft 38 or some other catheter component (instead of affixed to the guidewire introducer 10) and still be used to secure the guidewire 36 to the catheter 34 so that they may be advanced together.

Figure 3:
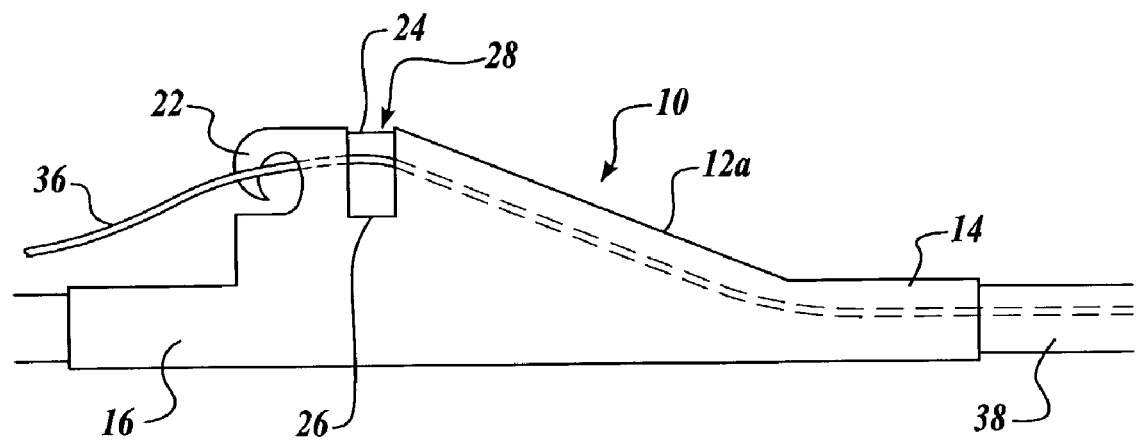
FIG. 3 is a side view of the guidewire introducer with locking device as shown in FIG. 2.

As shown in FIG. 2, guidewire lock 21 comprises a J-shaped catch 22 and a guiding tab 24. The J-shaped catch 22 has an entry end 23 and a locking end 25 and forms a corresponding J-shaped opening for receiving the guidewire 36. It will be appreciated by those skilled in the art that the J-shaped catch may be of any size or shape deemed suitable by the manufacturer or desired by the operator. For example, catch 22 may be of any shape or size so as to form an opening that is semi-circular, straight, angular, boot-shaped, etc. The opening may be of a diameter or width smaller than that of the guidewire 36 so as to further frictionally maintain the guidewire. In addition, the angle at which the entry end 23 of the catch 22 is disposed may also vary depending on manufacturing considerations, preferences of the operator, etc. For example, in the embodiment depicted in FIGS. 2 and 3, the entry end 23 of the J-shaped catch 22 is substantially parallel to the sleeve 16 of the guidewire introducer 10 (and hence, to the catheter 38). However, in other embodiments of the present invention, the entry end 23, locking end 25 and/or catch 22 itself may be at any angle relative to the catheter 38. Hence, the guidewire 36 could be secured in the catch 22 according to any operator preferences, such as preferences for positioning the guidewire 36, e.g., downwardly and away from the operator, upwardly toward the operator, etc.

Figure 4:
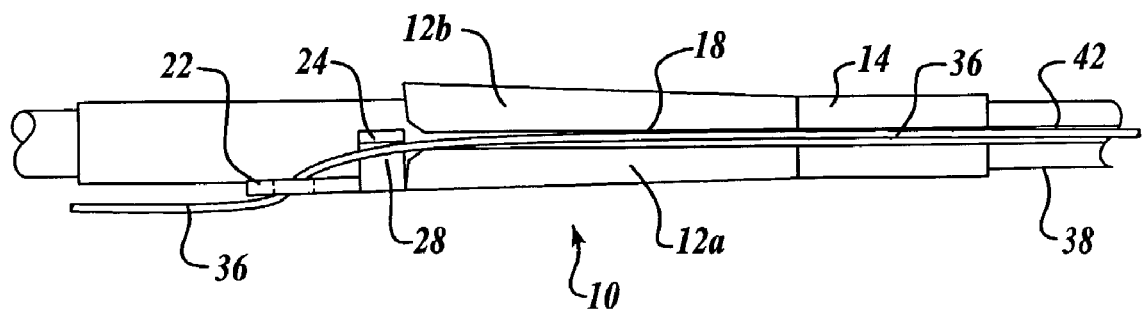
FIG. 4 is a top view of the guidewire introducer with locking device as shown in FIG. 2.

As shown in FIGS. 2 and 4, the J-shaped catch 22 is spaced apart from the proximal flange end 20 so as to form a generally rectangular shaped cut-out 26 between the J-shaped catch 22 and the proximal flange end 20. Accordingly, a guidewire receiving notch 28 is formed between the cut-out 26 and the L-shaped guiding tab 24 which extends away from the cut-out 26 and toward the opposing side 12b of the wedge-shaped flange 12. The L-shaped tab 24 serves to guide the guidewire 36 from the slot 18 to the catch 22 and constrain the guidewire to one side of the guidewire introducer 10, e.g., to the first side 12a of the flange 12. However, those skilled in the art will recognize that the guidewire receiving notch 28 and/or L-shaped tab 24 could be eliminated in some embodiments without departing from the spirit and scope of the present invention. In such embodiments the guidewire lock 21 would comprise the catch 22 without a further guiding or constraining device.

Once the guidewire 36 has been inserted into the C-shaped channel 42 of the shaft 38 via the slot 18 of the guidewire introducer 10, the operator may use the guidewire lock 21 as necessary to lock the guidewire 36 to the catheter 34 and advance the catheter and guidewire simultaneously. More specifically, an operator may direct the guidewire 36 through the slot 18, into the guidewire receiving notch 28 between the cut-out 26 and L-shaped tab 24, through the entry end 23 of the J-shaped catch 22 and into the locking end 25. Thus, the J-shaped catch 22 frictionally maintains the guidewire 36. Conversely, guidewire 36 can be released from the guidewire lock 21 by sliding guidewire 36 out of the J-shaped catch 22 and out of the guidewire receiving notch 28. Once released, the operator can advance or retract the guidewire independently of the catheter 34.

Although the embodiment described above and depicted in the drawings shows a guidewire introducer 10 with a guidewire lock 21 located on the first side 12a of the wedge-shaped flange 12 for ease of use by a right-handed operator, those skilled in the art will appreciate that the guidewire lock 21 may be positioned on the opposite side 12b of the guidewire introducer 10 for use by a left-handed operator. In fact, the guidewire lock 21 could be located anywhere on the guidewire introducer 10 depending on the application of the catheter, the preferences of the operator, etc. For example, the guidewire lock 21 may be located at any radial position about the catheter 34. Further, although the guidewire introducer 10, and thus, the guidewire lock 21, are depicted in FIG. 2 as mounted to the shaft 38 at the channel proximal end 52, it will be recognized that the guidewire lock 21 may be longitudinally positioned anywhere along the catheter 34. In yet other embodiments of the present invention, the guidewire introducer 10 may be equipped with a plurality of guidewire locks 21, again depending on the application of the catheter, the number of guidewires being used, the preferences of the operator, etc. For example, a guidewire lock 21 may be located on both sides 12a and 12b of the wedge-shaped flange 12 so that the operator could lock the guidewire 36 in either guidewire lock regardless of the operator's dexterity. As yet another example, a first guidewire lock could be located at the channel proximal end 52 and a second guidewire lock could be located between the channel proximal end 52 and proximal end 40 of the shaft 38.

While the preferred embodiment of the invention has been illustrated and described, it will be appreciated that various changes can be made therein without departing from the spirit and scope of the invention. For example, while the guidewire lock of the present invention is described above and shown as used with a cannulating device, the guidewire lock could also be used in any non-cannulating device that utilizes a guidewire, e.g., a device with an external lumen (i.e., a lumen next to the device). Further, the guidewire locking device of the present invention could also be used to lock two catheters together. In such embodiments, a boot-shaped catch with increased dimensions for receiving the larger catheter shaft may be used.

The embodiments of the invention in which an exclusive property or privilege is claimed are defined as follows:
1. A locking device comprising:
a catheter having a lumen and a channel for receiving and directing a guidewire into the lumen;
a catch fixedly mounted to the catheter adjacent the channel such that a guidewire received in the catch is aligned with the catheter channel, the catch selectively receiving and frictionally securing the guidewire to the catheter such that the catheter and guidewire may be advanced together; and wherein the catch comprises an entry end and a locking end, and wherein the entry end of the catch is positioned at substantially a right angle relative to the catheter.

2. A locking device comprising:

a catheter having a lumen and a channel for receiving and directing a guidewire into the lumen;

a catch fixedly mounted to the catheter adjacent the channel such that a guidewire received in the catch is aligned with the catheter channel, the catch selectively receiving and frictionally securing the guidewire to the catheter such that the catheter and guidewire may be advanced together; and further comprising a plurality of catches fixedly mounted to the catheter for selectively receiving the guidewire and frictionally securing the guidewire to the catheter.

3. A guidewire locking device connected to a guidewire introducer, the guidewire introducer being fixedly mounted to a catheter and used to introduce a guidewire into the catheter, the guidewire introducer having a slot defined therein that is aligned with an access channel in the catheter, the guidewire locking device comprising:

a first catch offset to one side of the slot, the catch comprising an entry end and a locking end, the entry end receiving the guidewire, and the locking end frictionally securing the guidewire to the catheter so that the guidewire and catheter may be advanced simultaneously; and further comprising a second catch offset to an opposite side of the slot from the first catch, the second catch having an entry end and a locking end, the entry end receiving the guidewire and the locking end securing the guidewire to the catheter so that the guidewire and catheter may be advanced simultaneously.

* * * * *

UNITED STATES PATENT AND TRADEMARK OFFICE
CERTIFICATE OF CORRECTION

PATENT NO. : 7,172,577 B2 Page 1 of 1
APPLICATION NO. : 10/217317
DATED : February 6, 2007
INVENTOR(S) : Michael J. Mangano et al.

It is certified that error appears in the above-identified patent and that said Letters Patent is hereby corrected as shown below:

Column 3
Line 42, delete "tat", and insert therefor -- that --.

Signed and Sealed this

Eighth Day of May, 2007

JON W. DUDAS
*Director of the United States Patent and Trademark Office*